United States Patent
Vo et al.

(10) Patent No.: US 11,723,687 B2
(45) Date of Patent: Aug. 15, 2023

(54) WINDOW DRESSING FOR USE WITH ULTRASONIC AID IN VENIPUNCTURE

(71) Applicant: Medline Industries, LP, Northfield, IL (US)

(72) Inventors: Nguyen S. Vo, Chicago, IL (US); Christopher R. Dalton, Mundelein, IL (US)

(73) Assignee: Medline Industries, LP, Northfield, IL (US)

( * ) Notice: Subject to any disclaimer, the term of this patent is extended or adjusted under 35 U.S.C. 154(b) by 529 days.

(21) Appl. No.: 16/710,627

(22) Filed: Dec. 11, 2019

(65) Prior Publication Data

US 2021/0177456 A1 Jun. 17, 2021

(51) Int. Cl.
| A61B 17/00 | (2006.01) |
| A61B 17/34 | (2006.01) |
| A61B 8/00 | (2006.01) |
| A61M 25/06 | (2006.01) |

(Continued)

(52) U.S. Cl.
CPC ........ *A61B 17/3403* (2013.01); *A61B 8/4281* (2013.01); *A61M 25/06* (2013.01); *A61B 2017/00889* (2013.01); *A61B 2017/00924* (2013.01); *A61B 2017/00951* (2013.01); *A61B 2017/3413* (2013.01); *A61B 2046/234* (2016.02); *A61M 2025/0166* (2013.01)

(58) Field of Classification Search
CPC ................ A61B 7/3403; A61B 8/4281; A61B 2017/00889; A61B 2017/00924; A61B 2017/00951; A61B 2017/3413; A61M 25/06; A61M 2025/0166
See application file for complete search history.

(56) References Cited

U.S. PATENT DOCUMENTS

| 4,556,066 A | 12/1985 | Semrow et al. |
| 5,394,877 A | 3/1995 | Orr et al. |
| 5,522,878 A | 6/1996 | Montecalvo et al. |
| (Continued) |

FOREIGN PATENT DOCUMENTS

| CN | 109069301 A | * 12/2018 | ....... A61F 13/00068 |
| EP | 3251601 B1 | 11/2018 | |
| (Continued) |

OTHER PUBLICATIONS

Parker Laboratories. Ultrasound-Guided Peripheral Intravenous Access (UGPIV), 2018.

*Primary Examiner* — Keith M Raymond
*Assistant Examiner* — Adam D. Kolkin
(74) *Attorney, Agent, or Firm* — Gurr Brande & Spendlove, PLLC.; Robert Spendlove

(57) ABSTRACT

A window dressing includes a primary layer having a window for viewing a catheter insertion site. The primary layer includes an adhesive layer on a lower, skin-contacting face of the primary layer. A transparent layer covers the window and adheres to the upper surface of the primary layer. An ultrasonic transmission layer is positioned below the primary layer, where the transmission layer comprises a layer of hydrogel. A support structure has a stiffness that is greater than the primary layer and has an adhesive layer on the lower surface of the support structure. The support structure adhesive layer adheres the support structure to the upper surface of the primary layer.

18 Claims, 16 Drawing Sheets

(51) Int. Cl.
*A61M 25/01* (2006.01)
*A61B 46/23* (2016.01)

(56) References Cited

U.S. PATENT DOCUMENTS

| | | | |
|---|---|---|---|
| 5,758,650 A | 6/1998 | Miller et al. | |
| 5,782,767 A | 7/1998 | Pretlow, III et al. | |
| 6,039,694 A | 3/2000 | Larson et al. | |
| 6,132,379 A | 10/2000 | Patacsil et al. | |
| 6,719,699 B2 | 4/2004 | Smith et al. | |
| 6,846,291 B2 | 1/2005 | Smith et al. | |
| 7,070,565 B2 | 7/2006 | Vaezy et al. | |
| 7,766,839 B2 | 8/2010 | Rogers et al. | |
| 8,043,604 B2 | 10/2011 | Wiley et al. | |
| 8,231,533 B2 | 7/2012 | Buchalter | |
| 8,882,673 B2 * | 11/2014 | Guzman | A61B 17/3468 604/528 |
| 8,961,936 B2 | 2/2015 | Wiley et al. | |
| 9,211,107 B2 | 12/2015 | Cox et al. | |
| 9,814,526 B2 | 11/2017 | Sloth et al. | |
| 10,064,599 B2 | 9/2018 | Desai et al. | |
| 10,206,653 B2 | 2/2019 | Desai et al. | |
| 2003/0149359 A1 * | 8/2003 | Smith | A61B 8/4281 600/437 |
| 2006/0030778 A1 * | 2/2006 | Mendlein | A61B 8/0858 600/437 |
| 2006/0058665 A1 | 3/2006 | Chapman et al. | |
| 2006/0184034 A1 | 8/2006 | Haim et al. | |
| 2006/0264751 A1 * | 11/2006 | Wendelken | A61B 8/4281 601/1 |
| 2008/0221519 A1 | 9/2008 | Schwach et al. | |
| 2008/0275396 A1 | 11/2008 | Neerken et al. | |
| 2009/0118670 A1 | 5/2009 | Neerken et al. | |
| 2010/0286521 A1 | 11/2010 | Betts | |
| 2011/0113886 A1 | 5/2011 | Elejalde et al. | |
| 2012/0232427 A1 * | 9/2012 | Bakema | A61B 7/04 600/586 |
| 2015/0141820 A1 | 5/2015 | Yamada | |
| 2015/0328434 A1 * | 11/2015 | Gaur | A61M 25/0026 600/424 |
| 2016/0270760 A1 | 9/2016 | Janicki et al. | |
| 2016/0296199 A1 * | 10/2016 | Mukherjee | A61B 46/10 |
| 2019/0099157 A1 | 4/2019 | Wagner et al. | |
| 2019/0133554 A1 | 5/2019 | Wagner et al. | |

FOREIGN PATENT DOCUMENTS

| | | |
|---|---|---|
| WO | 2015164708 A1 | 10/2015 |
| WO | 2006005351 A1 | 1/2016 |
| WO | 2017117817 A1 | 7/2017 |
| WO | 2019067350 A1 | 4/2019 |

* cited by examiner

WINDOW DRESSING FOR USE WITH ULTRASONIC AID IN VENIPUNCTURE

FIELD OF THE INVENTION

The present invention relates generally to medical dressings. More particularly, the invention relates to a window dressing with an ultrasound transmissive layer that secures a catheter at an insertion site and provides transmissivity for an ultrasonic transducer.

BACKGROUND OF THE INVENTION

In many instances, it is necessary to insert a catheter into a patient's skin. When performing this procedure, it may be difficult to find a vein or the desired vein to insert the catheter. Accordingly, as an aid when inserting a catheter, medical clinicians (e.g., doctors, nurses, and other medical personnel) may use an ultrasonic transducer to visualize the vein. This allows the medical clinicians to find the desired vein, and then insert the catheter through the patient's skin and into the vein. The use of ultrasound to guide catheter placement reduces the number of access attempts and may reduce other complications as well. Ultrasound guidance can be used for placing central venous catheters as well as for placing peripheral venous catheters.

An example of using current dynamic real time ultrasonic transducer guidance involves placing a coat of ultrasound gel over a general area that a catheter is to be placed; locating a vein by ultrasound via a connected monitor; introducing a catheter into the desired vein by observing the needle piercing the vein by ultrasound visualization; removing the needle, leaving the catheter in place; removing ultrasound gel from the site; and placing a window dressing over the site.

While existing methods may provide advantages, there remain inherent shortcomings. Examples of such shortcomings may include bacteria being transmitted from the ultrasonic transducer or the ultrasound gel into the patient at the catheter insertion site from ultrasonic transducers that may not be cleaned properly. Existing procedures may include the use of a barrier to prevent or reduce intrusion of non-sterile ultrasound gel into the catheter insertion site. However, the non-sterile ultrasound gel used in such procedures is not contained and can contaminate the catheter insertion site and surrounding environment. Due to the risk of contamination and other deficiencies of known methods, there is a need for a sterilized, self-contained gel window dressing or a sterile, self-contained gel covering that can be placed on an ultrasonic transducer and a corresponding procedure for catheter placement.

BRIEF DESCRIPTION OF THE FIGURES

Advantages of the invention will become apparent upon reading the following detailed description and upon reference to the drawings.

Figure 1:
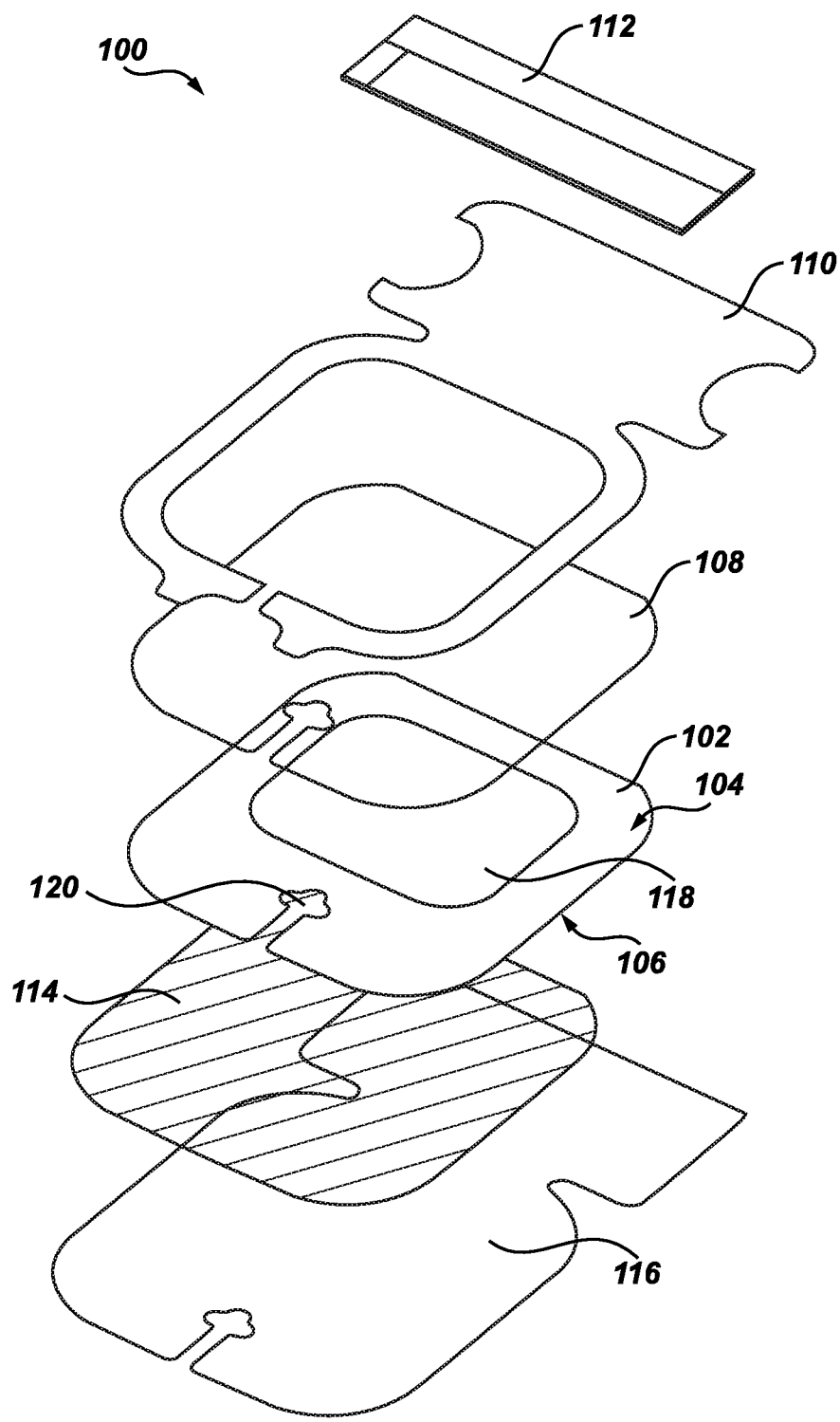
FIG. 1 is an exploded view of a preferred embodiment of a window dressing according to the present invention.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DETAILED DESCRIPTION

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, forward and rearward, proximal and distal, and the like may be used solely to distinguish one entity or action from another entity or action without necessarily requiring or implying any actual such relationship, direction or order between such entities or actions. As used herein, unless specifically indicated otherwise, the terms lower, below or proximal refer to a direction toward the patient's skin on which the dressing is used, and the terms upper, above or distal refer to a direction away from the patient's skin on which the dressing is used. Reference may also be made to longitudinal and latitudinal directions in reference to the window dressing described herein.

In one embodiment, as illustrated in FIGS. 1-4, a window dressing 100 may be used to secure a catheter inserted at a catheter insertion site. Such insertion sites may include a PICC ("peripherally inserted central venous catheter") insertion site, a jugular insertion site, a subclavian insertion site, a femoral insertion site, an implanted port insertion site, or any other similar insertion site. The window dressing 100 is capable of securing a variety of sizes, shapes, and types of catheters (single lumen, double lumen, triple, and quad lumen), infusion needles, and associated hubs, ports, and tubing. The window dressing 100 may provide protection against microbial ingress and site or patient systemic infection and may secure a catheter and associated hubs, ports, and tubing so that forces acting on the tubing and catheter do not peel the dressing from a patient's skin or cause the catheter to become dislodged. The window dressing 100, specifically an ultrasound transmissive layer 114, may also contain antimicrobial material that can provide additional protection against infection.

As further shown in FIGS. 1-4, a preferred embodiment of the window dressing 100 may comprise a primary layer 102 with an upper surface 104 and a lower surface 106. The window dressing 100 may comprise additional layers distal of the primary layer 102. These layers may include a transparent layer 108, a support structure 110, and one or more closure strips 112. The dressing 100 may further comprise additional layers proximal of the primary layer 102, including an ultrasound transmissive layer 114 and a release liner 116. The primary layer 102 may comprise a window 118 and a slot 120. The primary layer 102 may comprise a fabric material that may be a woven or nonwoven fabric. The fabric material may be formed from an appropriate material including manmade or naturally occurring fibers. Alternatively, the primary layer 102 may comprise a polymeric film. In various embodiments, the film or fabric layer may comprise plastic (PVC, polyethylene or polyurethane), latex, tape, cloth, paper or other materials. Still further, the primary layer 102 may comprise a combination of layers including fabrics or films or as well as coatings or additional supplemental materials. For example, the primary layer 102 may comprise materials having antimicrobial properties. The primary layer 102 as illustrated is generally square shaped with rounded corners; however, it is not limited to the illustrative shape. Accordingly, the primary layer 102 may come in many shapes, such as a circle, oval, rectangle, triangle, or any other shape. In addition, the size of the primary layer 102 may vary, such as a smaller size for a child and larger for an adult.

Figure 2:
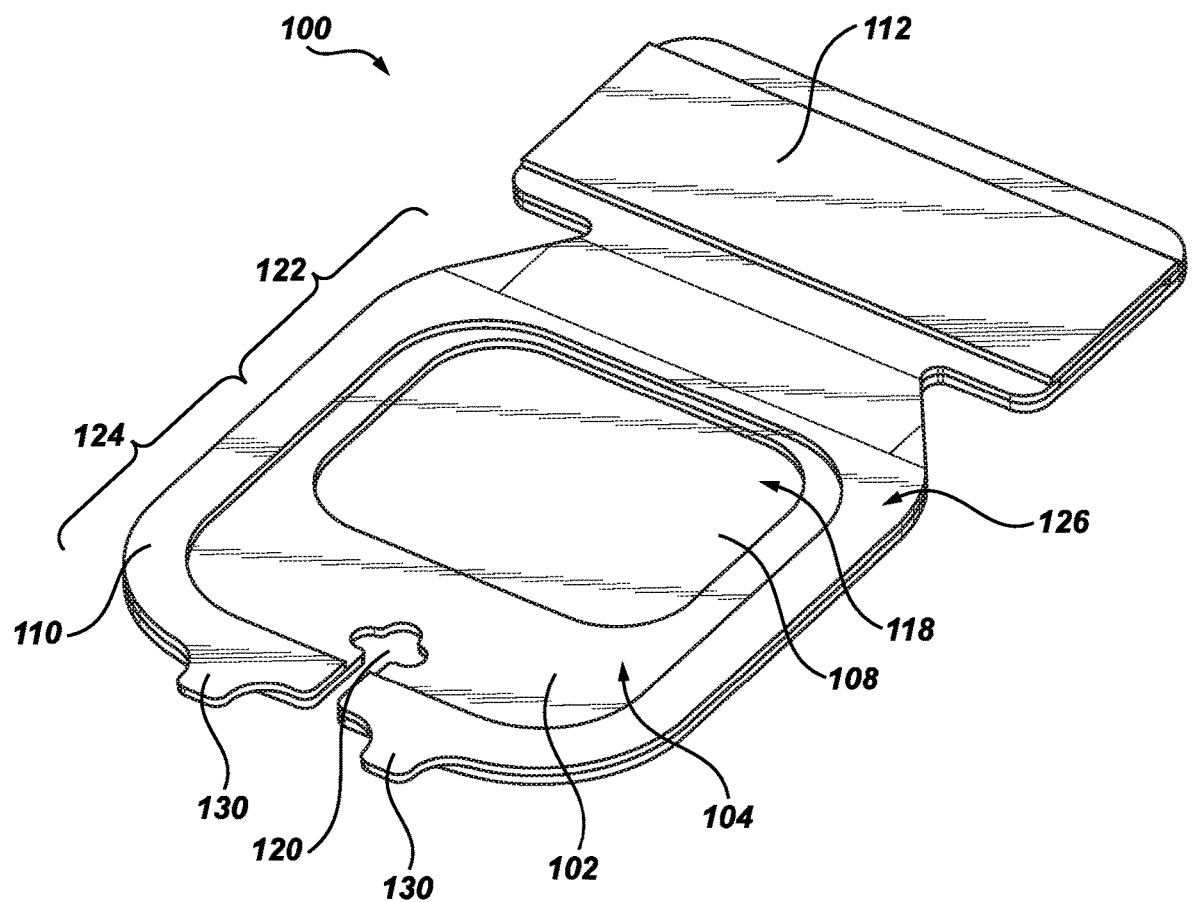
FIG. 2 is a perspective view of the window dressing of FIG. 1.
Figure 3:
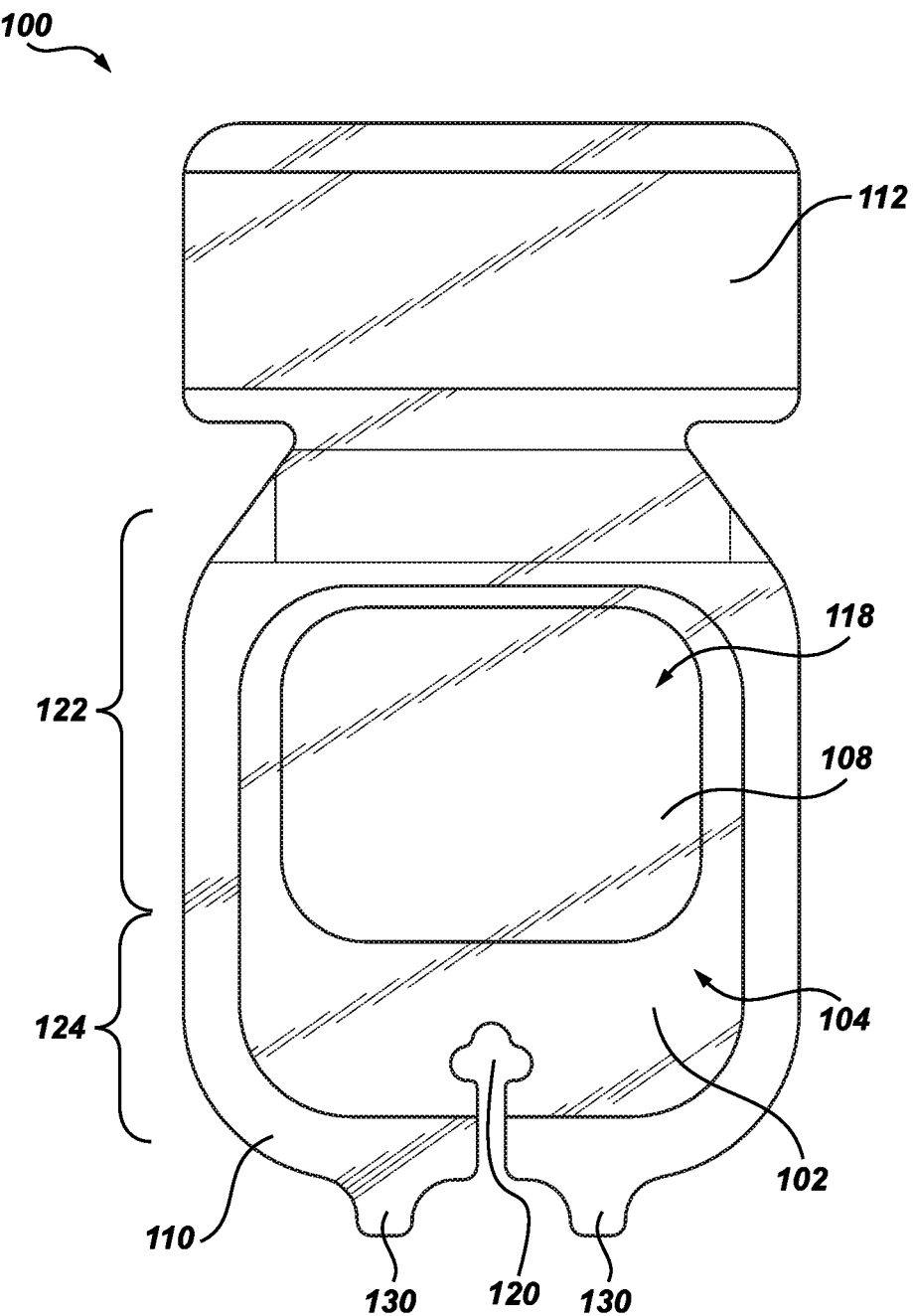
FIG. 3 is a top, plan view of the window dressing of FIG. 1.

Window 118 may be positioned within a window portion 122 of the dressing 100. The window 118 forms an opening that extends through the primary layer 102 forming a hole through the layer. The window 118 is positioned within the primary layer 102 such that the window 118 can be positioned around the insertion site when the dressing is applied to a patient. The window 118 may have a variety of shapes. For example, the window 118 may have a generally rectangular shape with rounded corners as illustrated in FIGS. 1-3. Alternatively, the window 118 may be domed shape. In further embodiments, the window 118 may be formed generally in the shape of a circle, half-circle, oval, square, triangle, polygon, crescent, or any other appropriate shape that allows the insertion site to be visible through the window 118.

In one embodiment of the window dressing 100, shown in FIGS. 1-4, a user positions the window 118 over the insertion site, and tubing (not shown) attached to the catheter is positioned beneath a securement portion 124 of the dressing 100. In this manner, the catheter site is visible through the window 118, and the tubing is secured to the patient's skin by the securement portion 124 of the dressing.

The securement portion 124 may comprise a slot 120. The slot 120 may extend inwardly from an edge of the primary layer 102. In a preferred embodiment, the slot 120 may be generally key shaped. Alternatively, the slot 120 may have a rectangular shape, U-shape, V-shape, or any other shape suitable to surround the catheter tubing. The slot 120 may be disposed in the securement portion 124 of the window dressing 100. The slot 120 may provide a location for tubing to exit from underneath the window dressing 100 and may help secure the tubing in place.

One or more closure strips 112, may be initially positioned on an upper or lower surface of the support structure 110. Alternatively, the closure strips 112 may be coupled to either the top or bottom surface of any other layer of the window dressing 100. The closure strips 112 may be detachably secured to the window dressing 100 with adhesive. These closure strips 112 may be detached and secured across the slot 120, and over the tubing to provide for increased securement of the tubing against the window dressing 100 or the patient's skin. Additionally, the closure strips 112 may also be placed underneath the tubing to further secure a side edge of the window dressing 100 against the patient's skin. Closure strips 112 may be formed from the same material as the window dressing 100 and may be provided along with the window dressing 100. Alternatively, the closure strips 112 may be a length of medical tape or another appropriate closure strip.

As illustrated in FIGS. 1-3, a transparent layer 108 may be positioned above the upper surface 104 of the primary layer 102. Alternatively, the transparent layer 108 may be positioned below the lower surface 106 of the primary layer. The transparent layer 108 may comprise a transparent film. The transparent film may be a polyurethane film. In some embodiments, the transparent layer 108 may have semipermeable characteristics. The transparent layer 108 may be a transmissive material so as to permit the sound waves from the ultrasonic transducer to penetrate the transparent layer 108 and ultrasound transmissive layer 114.

In embodiments of the window dressing 100, the transparent layer 108 may extend across all or a portion of the window portion 122 of the window dressing 100. In a preferred embodiment, the transparent layer extends across the entire area of the window portion 122, thereby securing the transparent layer 108 to the primary layer 102 and closing the window 118. The transparent layer 108 may have generally the same shape as the window 118. The transparent layer 108 may extend a distance beyond the periphery of the window 118 such that there is an area in which the transparent layer 108 overlaps with an upper surface 104 of the primary layer 102.

In an alternate embodiment of the window dressing 100, the transparent layer 108 extends across all or a portion of the securement portion 124 of the window dressing 100 in addition to extending across all or a portion of the window portion 122. In addition, the transparent layer 108 may be coextensive with the primary layer 102. Accordingly, in various embodiments, the transparent layer 108 covers the window 118 and is coupled to either the upper surface 104 or lower surface 106 of the primary layer 102.

The dressing 100 may further comprise a support structure 110 coupled to the transparent layer 108 and/or the primary layer 102. The support structure 110 may be a frame circumscribing the window 118 or in an alternative embodiment, may be coextensive with the primary layer 102. As illustrated, for example, in FIGS. 5-6, the support structure 110 may comprise a top surface 126 and a bottom surface 128. The support structure 110 may further comprise a support structure adhesive layer deposited on the bottom surface 128. The adhesive may be any suitable medical grade adhesive and may be coextensive with the bottom surface 128. Alternatively, the adhesive may extend across only a portion of the bottom surface 128 or may be applied in an alternating pattern of adhesive and non-adhesive areas. The support structure adhesive layer allows the support structure 110 to be adhered to the upper surface 104 of the primary layer 102 and/or the transparent layer 108. Further, the support structure 110 may releasably adhere to the window dressing 100 and be removed once the window dressing 100 is placed on a patient's skin.

Embodiments of the support structure 110 may comprise a material that has a higher stiffness than the primary layer 102. For example, the support structure 110 may comprise a polyester film. Preferably, the support structure 110 has a thickness between 0.005 and 0.100 inches, more preferably between 0.005 and 0.030, more preferably between 0.005 and 0.015, or yet more preferably having a thickness of 0.01 inches. The support structure 110 may be transparent or may have a color, texture or other property to visually distinguish the support structure 110 from the primary layer 102 of the window dressing 100. For example, the support structure 110 may be transparent, translucent or opaque in combination with various levels of coloration.

Further, as shown in FIGS. 1-3, the support structure 110 may have tabs 130. While a plurality of tabs may be used, it should be appreciated that embodiments using one tab are also contemplated. The tabs 130 provide a place that the user may grasp to pull the support structure 110 away from the transparent layer 108 and primary layer 102 after the window dressing 100 is attached to a patient. The tabs 130 can be visible protrusions, or alternatively, a lip that slightly overhangs the primary layer 102. The tabs 130 may be a different color or texture to be distinguished from the support structure 110.

Embodiments of the window dressing 100 may comprise an adhesive layer 132 (shown, e.g., in FIG. 6) disposed on a lower, skin-facing surface of the dressing 100. The adhesive layer 132 is exposed and able to adhere to a patient's skin once the release liner 116, discussed below, has been discarded. The adhesive may comprise any suitable medical adhesive. For example, the adhesive may be an acrylate, including methacrylates and epoxy diacrylates. Alternatively, the adhesive may be a silicone based adhesive. In embodiments of the invention, the adhesive may be coextensive with the lower surface 106 of the primary layer 102.

Figure 4:
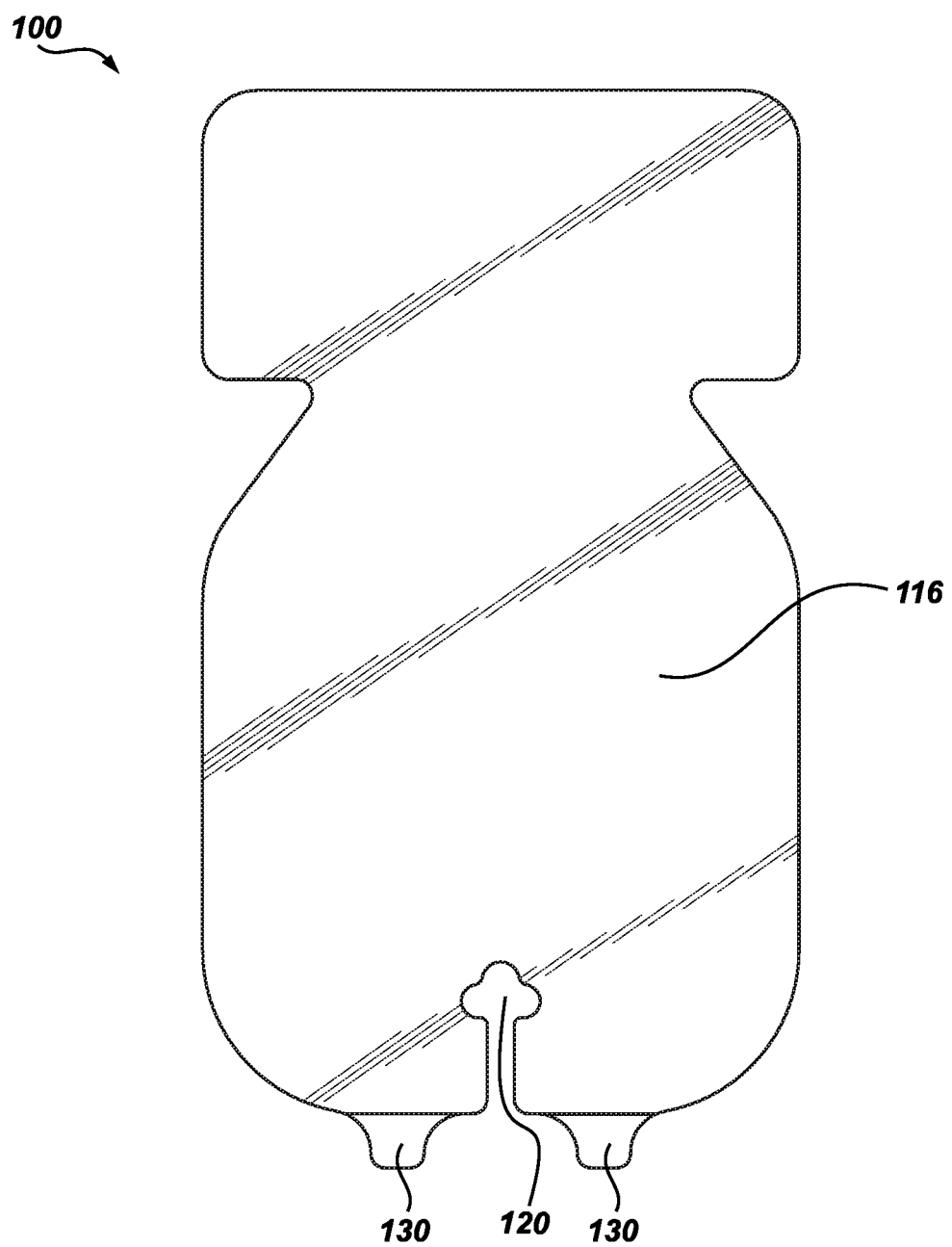
FIG. 4 is a bottom, plan view of the window dressing of FIG. 1.

As can be seen in FIG. 4, the window dressing 100 may further comprise a release liner 116. The release liner 116 may adhere or releasable adhere to a lower surface of the window dressing 100, including to the lower surface 106 of the primary layer 102, the adhesive layer 132, ultrasound transmissive layer 114, discussed below, or to some combination of these or other layers. The release liner 116 may extend across all or part of the proximal surface of the window dressing 100. The release liner 116 may protect the adhesive layer 132 and/or ultrasound transmissive layer 114 from prematurely adhering to an undesired location and may be removed from the window dressing 100 prior to application onto the patient's skin in order to expose the adhesive layer 132 and/or ultrasound transmissive layer 114.

Figure 5:
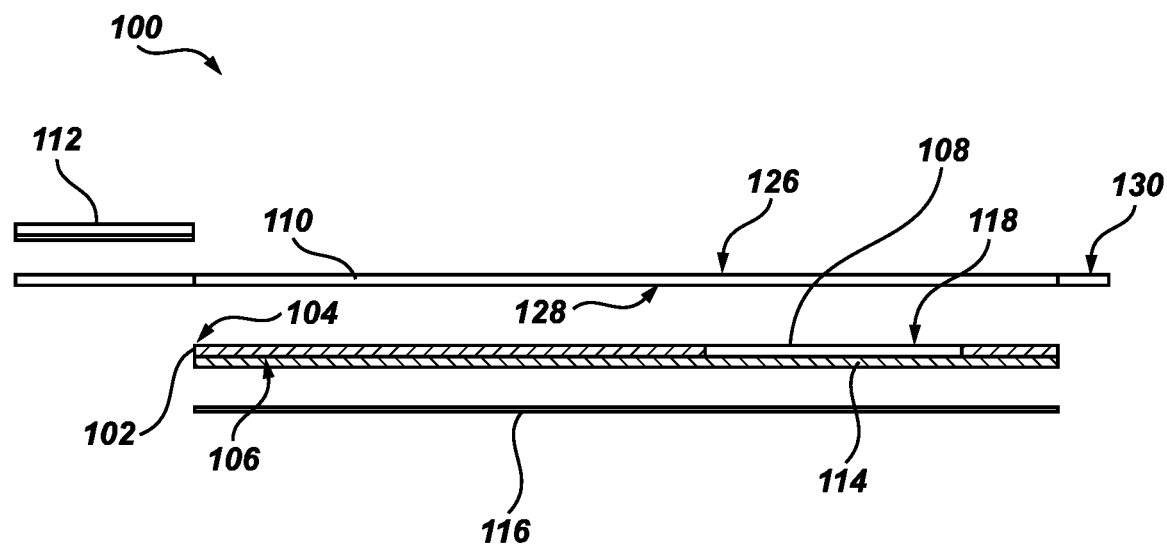
FIG. 5 is a cross-sectional view of a window dressing with an ultrasound transmissive layer coextensive with a primary layer.
Figure 6:
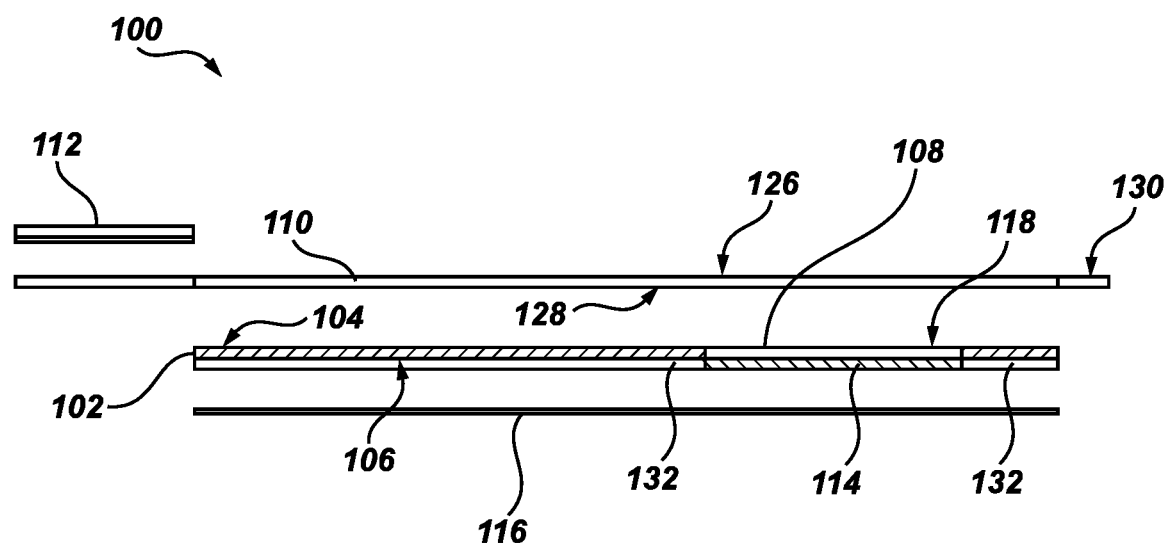
FIG. 6 is a cross-sectional view of a window dressing with an ultrasound transmissive layer and adhesive layer on a lower surface of a primary layer

Referring to FIGS. 5-6, an ultrasound transmissive layer 114 may be positioned between the lower surface 106 of the primary layer 102 and the release liner 116. The ultrasound transmissive layer 114 acts as a layer that is transmissive to ultrasonic sound waves as used in diagnostic sonography or other medical ultrasound techniques. The ultrasound transmissive layer 114 may preferably comprise hydrogel, and the term hydrogel layer 114 is used interchangeably with ultrasound transmissive layer 114 herein. However, it should be understood that other transmissive gels, liquids, or other materials may be used and self-contained in the window dressing 100. The ultrasound transmissive layer 114 may be in an even layer that is self-contained and deposited on a lower surface of a window portion 122. Alternatively, it may only be found directly below the transparent layer 108 covering the window 118 or generally covering the window 118 but extending beyond the periphery of the window 118. In a further alternative, the ultrasound transmissive layer 114 may be coextensive with the primary layer 102.

The ultrasound transmissive layer 114 may come in a variety of thicknesses as would be understood by one of ordinary skill in the art. Preferably, the ultrasound transmissive layer 114 has a thickness between 0.02 and 5 millimeters, preferably between 0.2 and 4 millimeters, more preferably between 1 and 3 millimeters, or yet more preferably having a thickness of 1 millimeters.

Figure 7:
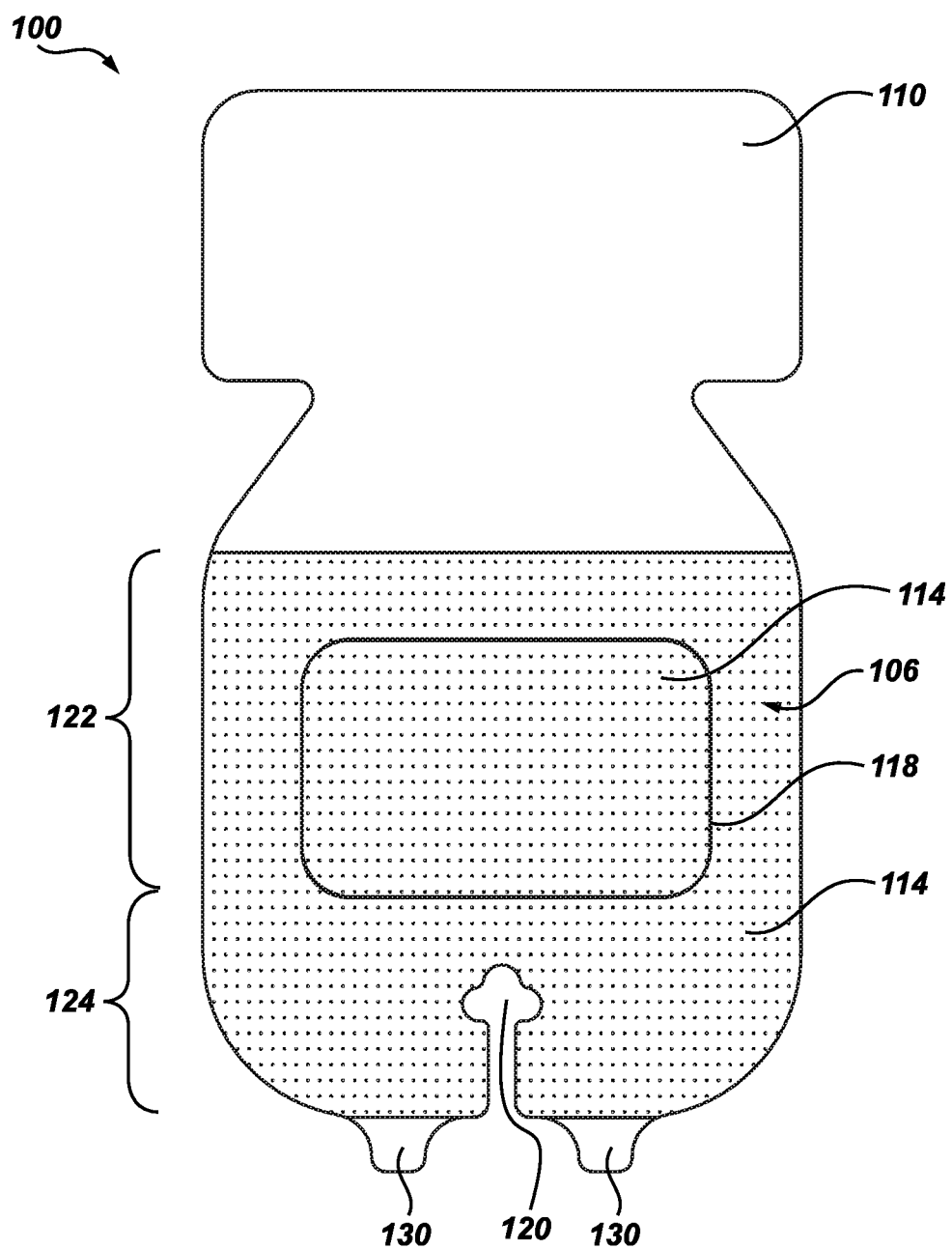
FIG. 7 is a bottom, plan view of a window dressing with an ultrasound transmissive layer.

The ultrasound transmissive layer 114 may have adhesive qualities, and thereby it may act as an adhesive to adhere the window dressing 100 to the patient. For example, the window dressing 100 may comprise the release liner 116 that releasably adheres to the ultrasound transmissive layer 114. Once the release liner 116 is removed, as shown in FIG. 7, the ultrasound transmissive layer 114 can adhere to a patient, without the need of an adhesive layer 132.

Figure 8:
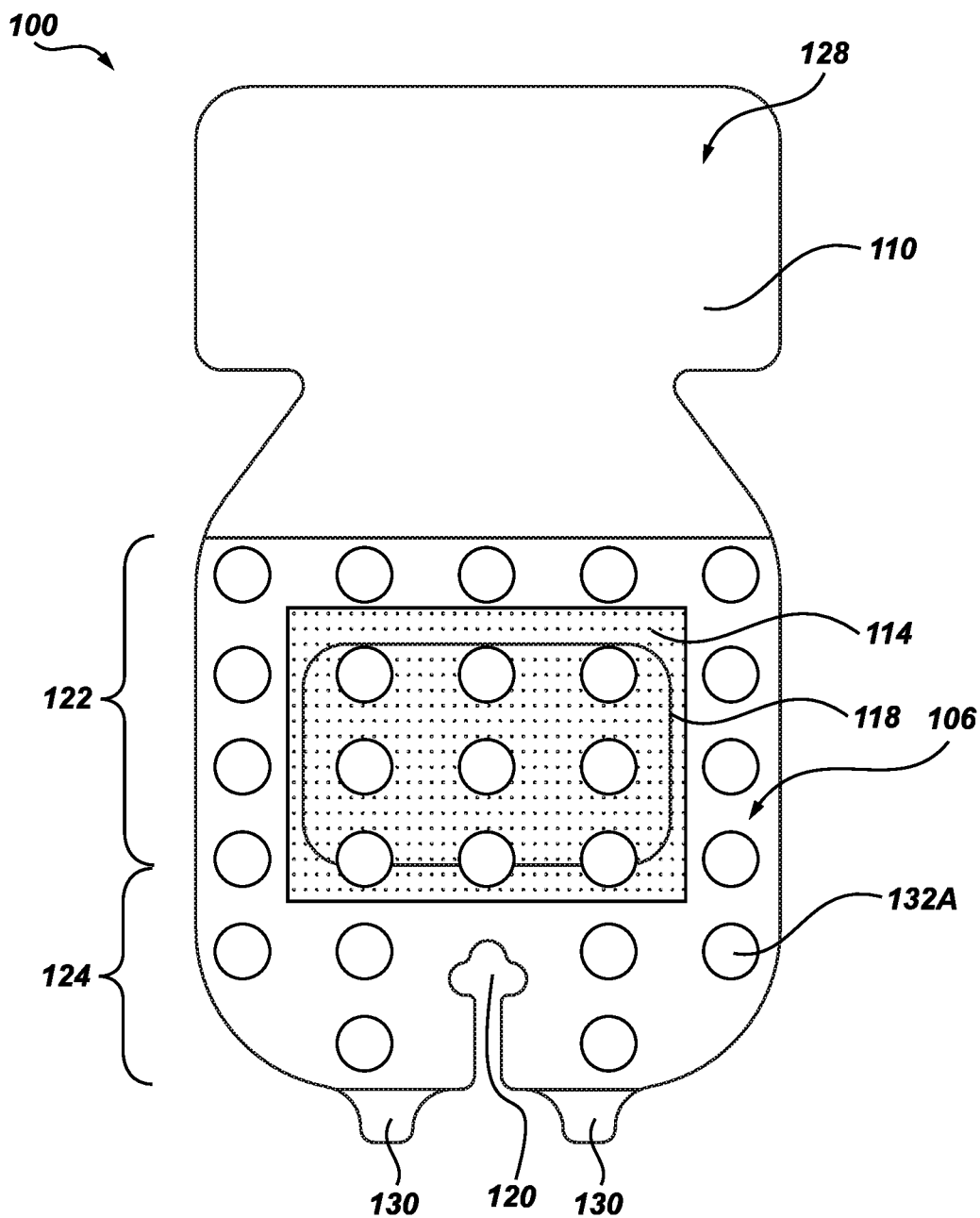
FIG. 8 is a bottom, plan view of a window dressing with an ultrasound transmissive layer with an alternating pattern of adhesive.

Alternatively, the ultrasound transmissive layer 114 may be used in conjunction with the adhesive layer 132. In embodiments of the dressing, the adhesive may extend across only a portion of the lower surface 106 of the primary layer 102. For example, as shown in FIG. 8, the ultrasound transmissive layer 114 may extend across a portion of the proximal surface of the window dressing 100. Adhesive layer 132 may then be applied to a proximal surface of the dressing in an alternating pattern of adhesive 132A. FIG. 8 illustrates the adhesive applied in a dot pattern, but other shapes and patterns are contemplated. As shown, the adhesive pattern 132A may be applied to areas covered by the ultrasound transmissive layer 114 and/or to areas of the primary layer 102 lower surface 106 that are not covered by the ultrasound transmissive layer 114. Further, the ultrasound transmissive layer 114 may be deposited in areas that the adhesive, on the lower surface 106 of the primary layer 102, is not found. For example, an adhesive layer on the lower surface 106 that circumscribes the window dressing 100 can have hydrogel deposited within the void created by the adhesive.

Figure 9:
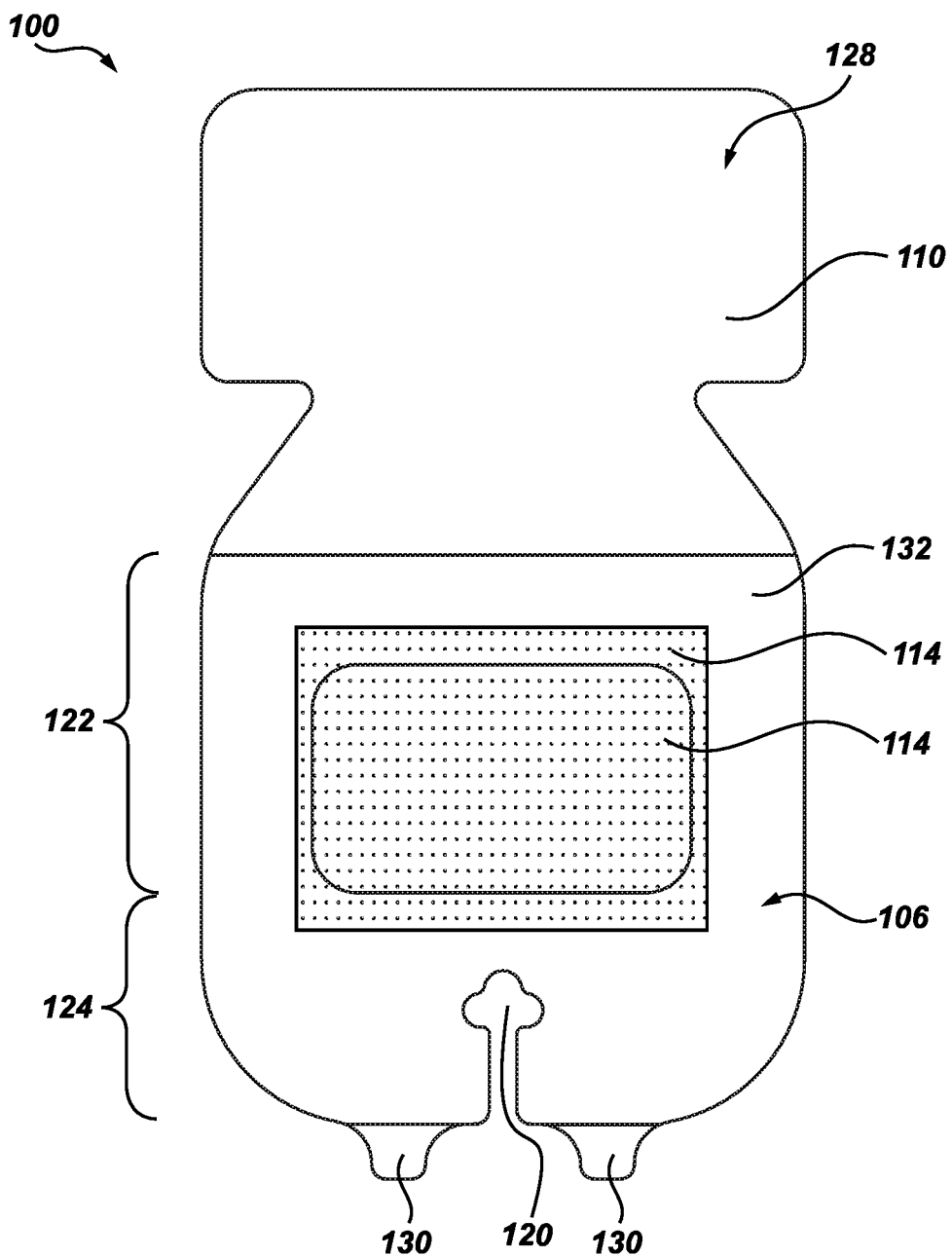
FIG. 9 is a bottom, plan view of a window dressing with an adhesive layer surrounding a window portion with an ultrasound transmissive layer.
Figure 10:
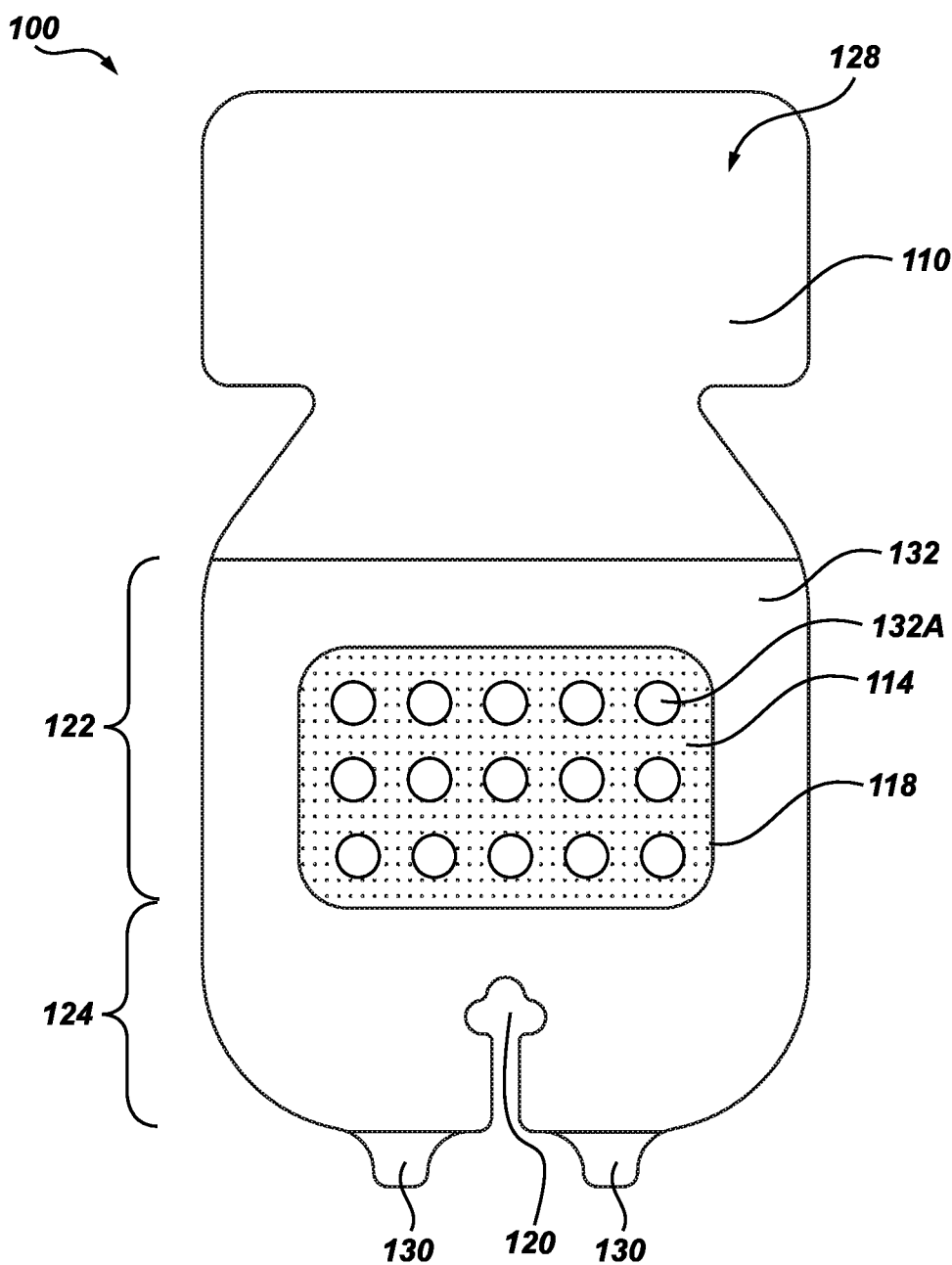
FIG. 10 is a bottom, plan view of a window dressing with an adhesive layer surrounding a window and an alternating pattern of adhesive in an ultrasound transmissive layer.
Figure 11:
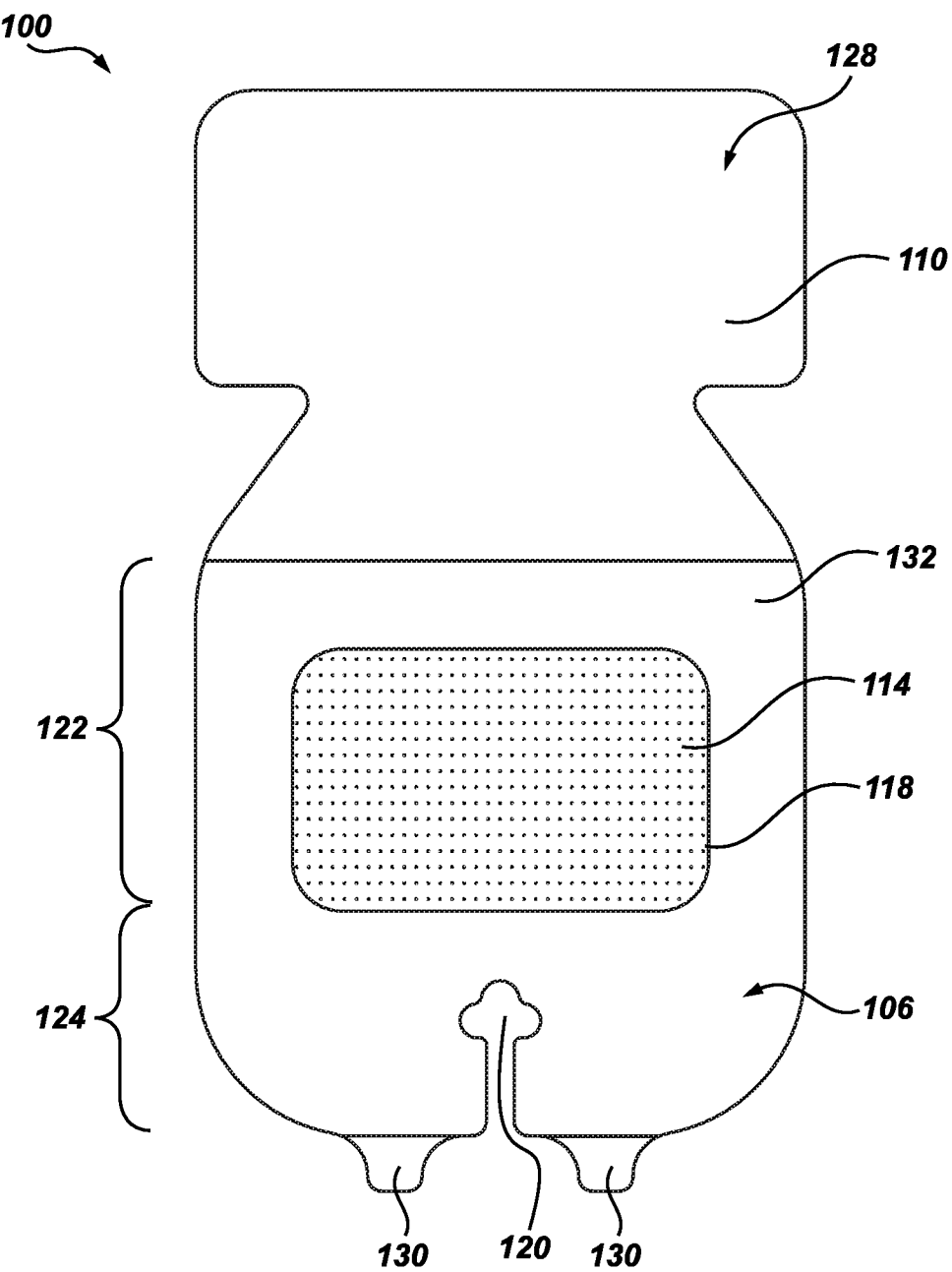
FIG. 11 is a bottom, plan view of a window dressing with an adhesive layer surrounding an ultrasound transmissive layer deposited in a window.

Alternatively, as illustrated in FIG. 9, the adhesive layer 132 may circumscribe the window portion 122 having the ultrasound transmissive layer 114. In further embodiments, illustrated in FIG. 10, the adhesive layer 132 may circumscribe the window 118 as well as be inserted in an alternating pattern of adhesive 132A in ultrasound transmissive areas within the window 118. It will be appreciated that the adhesive layer 132 surrounding the window 118 may act as an additional barrier to prevent bacteria and other contaminates from reaching the insertion site. In further embodiments, illustrated in FIG. 11, the adhesive layer 132 may circumscribe the window 118 having the ultrasound transmissive layer 114.

Having an ultrasound transmissive layer 114 in the window dressing 100, removes the need for placing a non-sterile coat of ultrasound gel over the general area where the catheter is to be placed. The ultrasound transmissive layer 114 acts as a transmissive layer for the ultrasonic device. It will be appreciated that the ultrasound transmissive layer 114 may provide multiple advantages, including being self-contained and preventing a potential physical mess and contamination. The ultrasound transmissive layer 114 may further have anti-microbial material that can assist in providing a clean environment for the catheter site and ensure healing. Examples of anti-microbial material include but are not limited to silver, chlorhexidine, or polyhexamethylene biguanide. Further, the catheter insertion site may be completely covered by the ultrasound transmissive layer 114, which helps prevent bacteria from entering the insertion site via the ultrasonic transducer or other non-sterile medical instruments.

Figure 12:
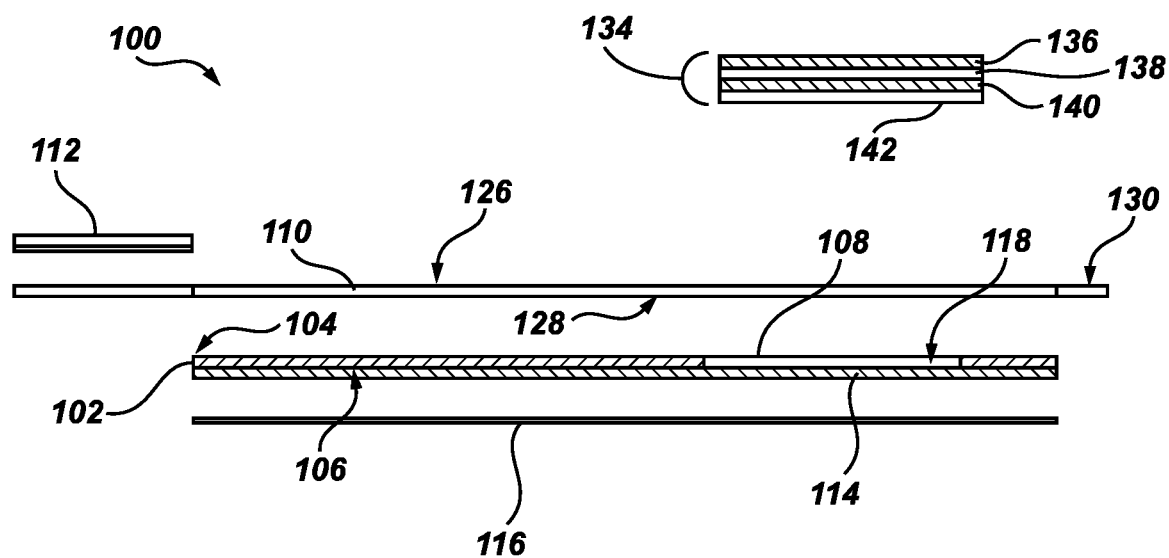
FIG. 12 is a cross-sectional view of a window dressing with a pad.

Referring to FIG. 12 and as discussed above, embodiments of the dressing 100 may comprise a pad 134 positioned above the upper surface 104 of the primary layer 102. The pad 134 may be coupled to the support structure 110 and/or the transparent layer 108 and may extend across all or a portion of the window 118. The pad 134 may be commensurate in size to the window portion 122, or the pad 134 may be coextensive with the primary layer 102. The pad 134 may comprise a top occlusive layer 136, a middle liquid layer 138, and a bottom occlusive layer 140. The middle liquid layer 138 may be any liquid or gel that assists in the transmission of ultrasonic sound waves. The pad 134 may be used in conjunction with the ultrasound transmissive layer 114. A removably attachable adhesive layer 142 may be deposited on a lower surface of the pad 134. Further, the pad 134 may vary in materials and may have a thickness that is relatively thinner or thicker than the primary layer 102.

As will be understood, the pad 134 may add an extra transmissive layer, with the ultrasound transmissive layer 114, for transmissivity for an ultrasonic device to assist a user in finding the desired vein when inserting a catheter. The pad 134 may be removable by decoupling the pad 134, with the removably attachable adhesive layer 142, after the ultrasound has been performed. For example, once the user has found the correct vein and has inserted the catheter, the user then may discard the pad 134 by removing the pad 134 alone or by removing the support structure 110 with the pad 134 coupled thereto. The pad 134 may be provided coupled to the window dressing 100 or it may be provided as a separate component that is attached by the medical practitioner upon application of the window dressing 100. It will also be appreciated that the liquid layer 138, in the pad 134, is self-contained. As discussed above with regard to the ultrasound transmissive layer 114, having a self-contained pad 134 provides advantages over the prior art with respect to containment of potential liquid leakage and corresponding reduction of infection risk.

Further, FIG. 12 illustrates embodiments of the window dressing 100 in a disassembled state prior to use. The transparent layer 108, the support structure 110, the closure strips 112, and the pad 134 are positioned above the distal surface 104 of the primary layer 102. The pad 134 further comprises a top occlusive layer 136, a middle liquid layer 138, and a bottom occlusive layer 140, which together couples to the support structure 110 and/or the transparent layer 108. The transparent layer 108 adheres to the upper surface 104 of the primary layer 102 at those points where the transparent layer 108 is in contact with the upper surface 104. Embodiments of the transparent layer 108 are flexible, and the transparent layer 108 conforms to the surface of the primary layer 102.

Figure 13:
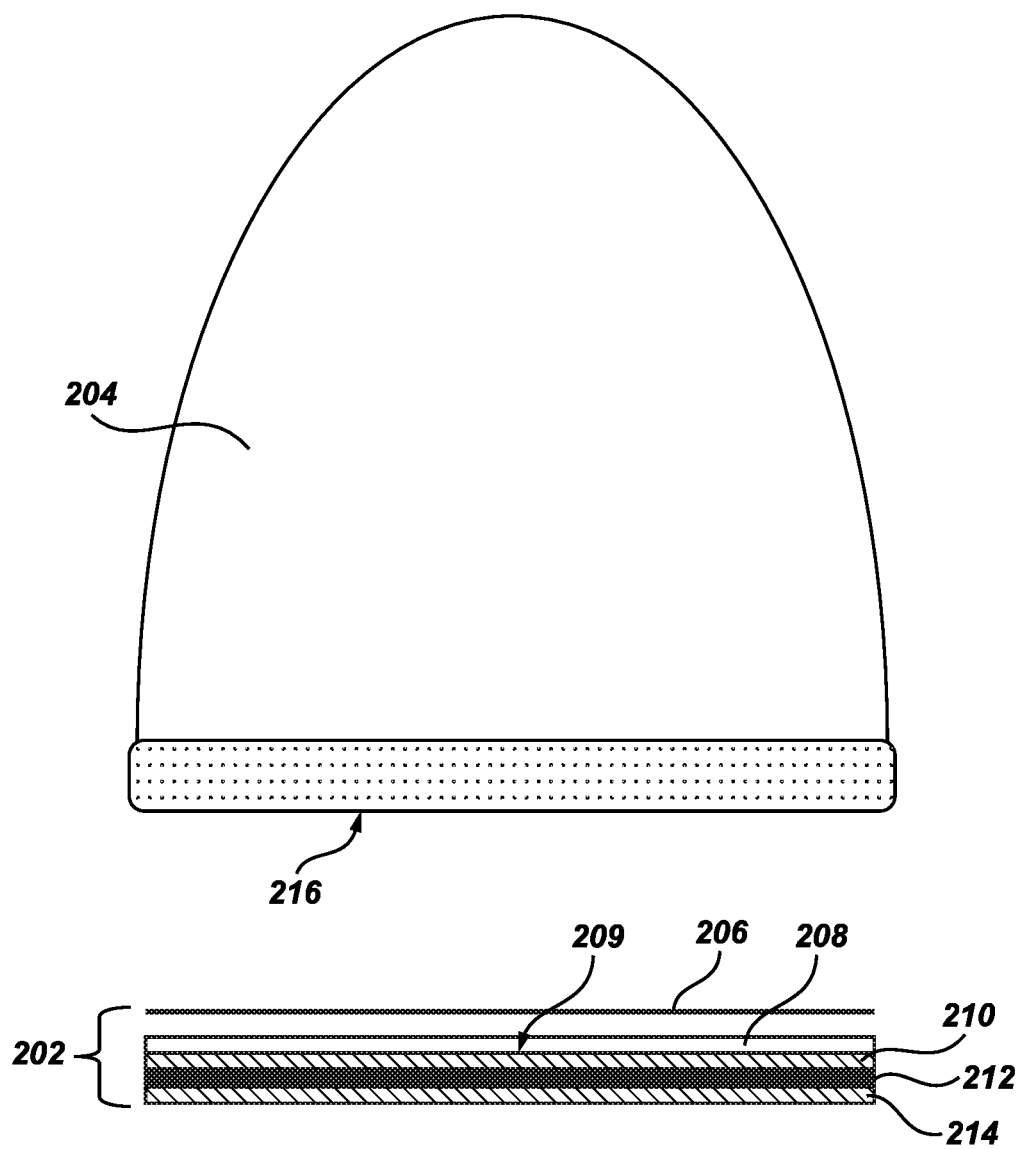
FIG. 13 is a cross-sectional view of an ultrasonic transducer pad detached from an ultrasonic transducer.
Figure 14:
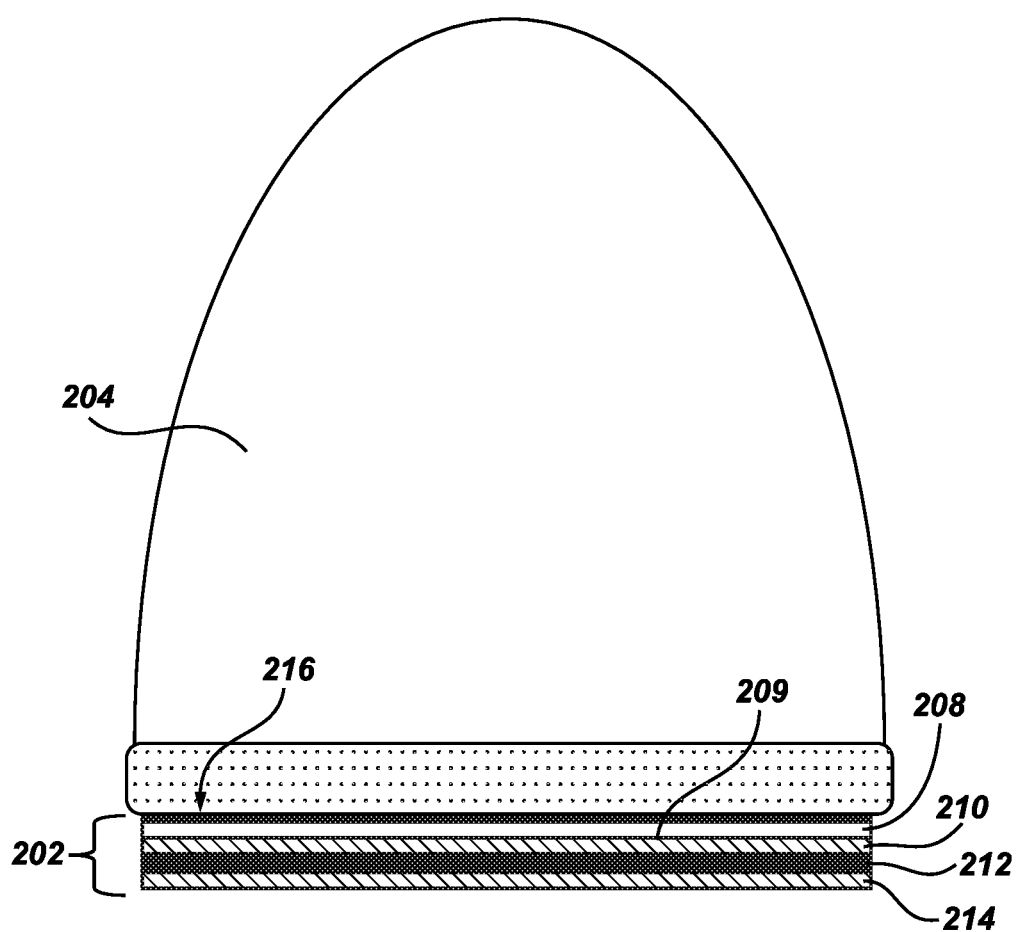
FIG. 14 is a cross-sectional view of an ultrasonic transducer pad attached to an ultrasonic transducer.

As shown in FIGS. 13-14, in further embodiments, an ultrasonic transducer pad 202 can be attached by a medical practitioner to an ultrasonic transducer 204. The ultrasonic transducer pad 202 may come as part of a kit with the window dressing 100 or may be provided as a separate component. The ultrasonic transducer pad 202 may resemble the layers in the pad 134 illustrated in FIG. 12. The ultrasonic transducer pad 202 may comprise a release liner 206, an adhesive layer 208, a first occlusive layer 210, a liquid layer 212, and a second occlusive layer 214. The liquid layer 212 may be any liquid or gel that assists in the transmission of ultrasonic sound waves. It will be understood that other layers may be utilized in the ultrasonic transducer pad 202. The ultrasonic transducer pad 202 may be coextensive with an ultrasonic transducer attachment site 216 (as shown in FIGS. 13-14). The release liner 206 is in a position to protect the adhesive layer 208 prior to coupling it to the ultrasonic transducer 204. The adhesive layer 208 is positioned on an upper surface 209 of the first occlusive layer 210. The adhesive layer 208 may extend across the upper surface 209 of the first occlusive layer 210 or may be applied in an alternating pattern of adhesive and non-adhesive areas. The first and second occlusive layers 210, 214 contain the liquid layer 212, which allows for increased transmissivity to aid in finding a patient's vein.

It should be appreciated that the ultrasonic transducer pad 202 may be used without the window dressing 100. For example, the ultrasonic transducer pad 202 may be used for other diagnostic sonography procedures beyond catheter placement. The ultrasonic transducer pad 202 may be used anytime it is desired to provide a self-contained object which can aid in transmissivity of ultrasound waves. The ultrasonic transducer pad 202 may be removed and replaced for additional procedures. It will be appreciated that the ultrasonic transducer pad 202 comprises a self-contained structure, which provides similar advantages to those discussed above with regard to the use of hydrogel in the window dressing 100.

Figure 15:
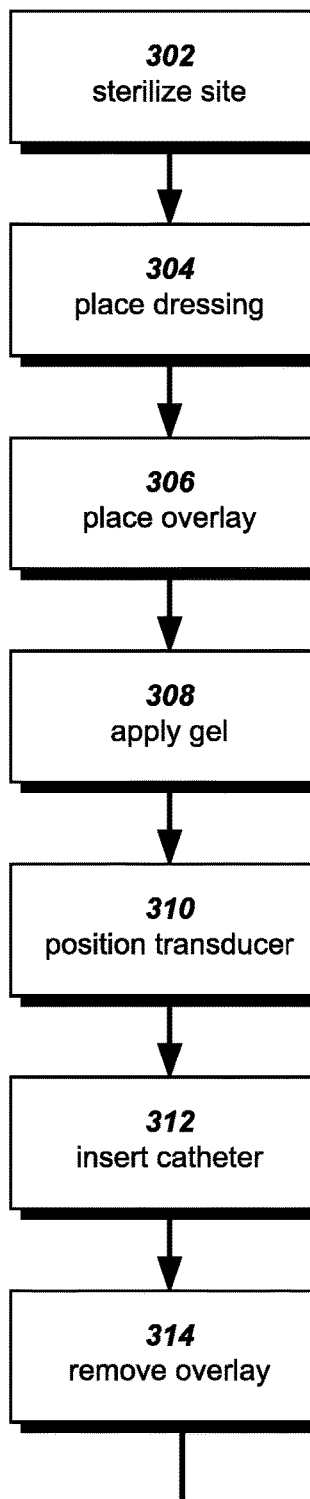
FIG. 15 is a schematic representation of a method of using an ultrasonic transducer for aid in venipuncture in accordance with methods known in the prior art.
Figure 15:
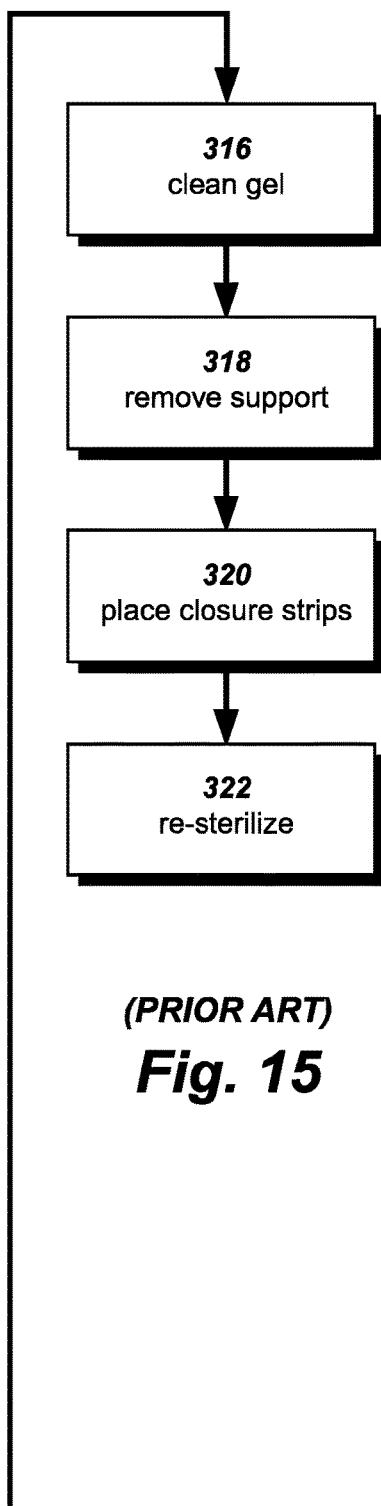

Currently known methods of placing a catheter with sonographic assistance require several steps devoted to uncontained gel management. As illustrated in FIG. 15, currently known methods require at least the following steps: (1) Sterilize the catheter insertion site with a conventional disinfectant such as Chlorhexidine Gluconate (CHG) or Isopropyl Alcohol (IPA) 302; (2) remove a release liner and place a window dressing having a support structure and closure strips on the site 304; (3) place an overlay on the site 306; (4) coat the top of the overlay with an ultrasound gel 308, in the known method, the gel is squeezed from a tube of gel onto a top surface of the overlay; (5) position an ultrasound transducer in the gel coating the overlay 310; (6) insert and position the catheter with the aid of ultrasonic visualization 312; (7) remove the overlay, leaving a sterile dressing and catheter in place 314; (8) clean any gel that has migrated beyond the overlay 316; (9) remove the support structure from the dressing 318; (10) remove closure strips from support structure and place strips over the catheter tube to prevent movement of the catheter 320; and (11) sterilize the area as necessary due to any contamination by the uncontained gel 322.

Figure 16:
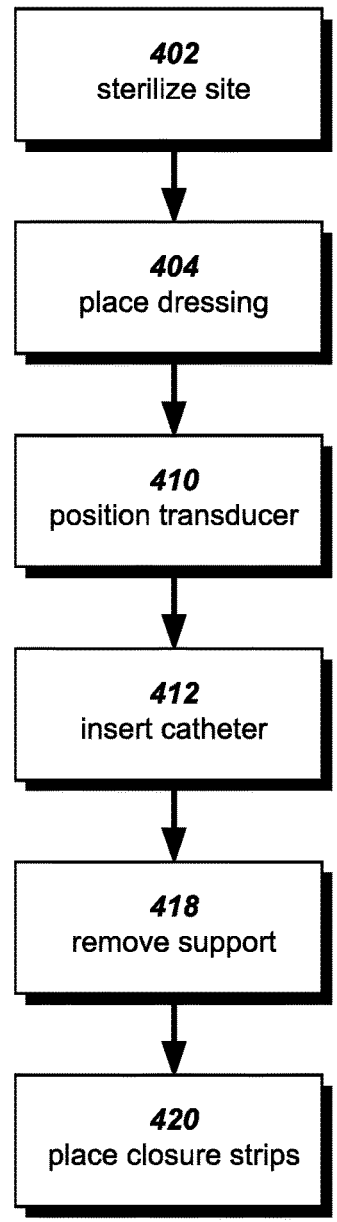
FIG. 16 is a schematic representation of a method of using an ultrasonic transducer for aid in venipuncture.

In contrast, methods using embodiments as disclosed herein do not require such steps. As illustrated in FIG. 16, methods employing disclosed embodiments require the following steps: (1) Sterilize the catheter insertion site with a conventional disinfectant such as Chlorhexidine Gluconate (CHG) or Isopropyl Alcohol (IPA) 402; (2) remove a release liner from the window dressing and place the window dressing at least partially on the site 404; (3) position an ultrasound transducer on top of the self-contained dressing that is contacting the skin 410; (4) insert and position the catheter with the aid of ultrasonic visualization 412; (5) remove the support structure from the dressing 418; and (6) remove closure strips from support structure and place strips over the catheter tube to prevent movement of the catheter 420.

Figure 17:
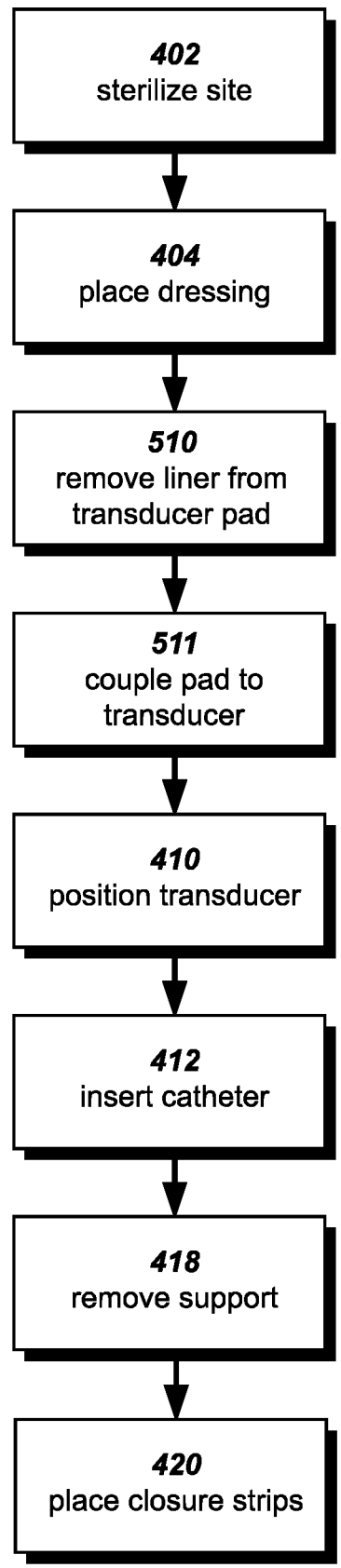
FIG. 17 is a schematic representation of a further method of using an ultrasonic transducer for aid in venipuncture.

Alternatively, as illustrated in FIG. 17, a method may include additional steps incorporating a transducer pad (202) onto the transducer 204 to aid in transmissivity of ultrasound waves. In this method, including a step 510 in which a user may remove a release liner (206) from an ultrasonic transducer pad (202) and a step 511 in which a user couples the transducer pad (202) to an ultrasonic transducer attachment site (216). The user can then place the ultrasonic transducer (204) onto the window dressing (100) in step 410 and find the desired vein to insert a catheter in step 412. Other steps may correspond to the steps set out above with regard to the method illustrated in FIG. 16.

While the present invention has been described with reference to one or more particular embodiments, those skilled in the art will recognize that many changes may be made thereto without departing from the spirit and scope of the present invention. Furthermore, components from one embodiment can be used in other non-exclusive embodiments. Each of these embodiments and obvious variations thereof is contemplated as falling within the spirit and scope of the invention.

What is claimed is:

1. A window dressing for ultrasonic aid in venipuncture comprising:
    a primary layer having a lower surface and an upper surface, the primary layer further comprising a window portion and a securement portion;
    a release liner covering at least a portion of the lower surface of the primary layer;
    an ultrasound transmissive layer having a lower surface and an upper surface, the ultrasound transmissive layer disposed between the lower surface of the primary layer and the release liner;
    a transparent layer coupled to the primary layer and covering at least a portion of the window in the primary layer; and
    a support structure, wherein the support structure is coupled to the transparent layer and the primary layer, wherein the window dressing secures a catheter at a catheter insertion site via the securement portion.

2. The window dressing of claim 1, wherein the ultrasound transmissive layer comprises a hydrogel.

3. The window dressing of claim 1, further comprising an adhesive layer disposed between the lower surface of the primary layer and the release liner.

4. The window dressing of claim 3, wherein the adhesive layer is coextensive with the primary layer.

5. The window dressing of claim 1, wherein the transparent layer covers the entire window of the primary layer and the transparent layer is coupled to a portion of the upper surface of the primary layer.

6. The window dressing of claim 5, wherein the transparent layer further covers the securement portion of the primary layer.

7. The window dressing of claim 1, wherein the support structure circumscribes the primary layer window.

8. The window dressing of claim 1, wherein the support structure is coextensive with the primary layer.

9. The window dressing of claim 1, further comprising a pad, the pad comprising a top occlusive layer, a middle layer comprising a transmissive material, and a bottom occlusive layer.

10. The window dressing of claim 9, wherein the middle layer is sealed between the top and bottom occlusive layers.

11. The window dressing of claim 9, wherein the middle layer comprises a liquid.

12. The window dressing of claim 1, wherein the primary layer comprises a closure strip.

13. The window dressing of claim 1, wherein the ultrasound transmissive layer comprises antimicrobial material.

14. The window dressing of claim 1, wherein the ultrasound transmissive layer is deposited on a window portion of the lower surface of the primary layer.

15. A method of applying a window dressing and inserting a catheter with the aid of an ultrasonic transducer, the method comprising:
    identifying a catheter insertion site where the catheter is to be inserted;
    removing a release liner from the window dressing exposing a lower surface of the window dressing;
    placing a window of the window dressing at least partially over the catheter insertion site;
    positioning an ultrasound transducer in contact with an upper surface of the window dressing such that sound waves emitted by the ultrasound transducer pass through an ultrasound transmissive layer of the window dressing;
    locating a vein based at least in part on information obtained from the ultrasound transducer;
    inserting a needle and catheter into the located vein;
    removing the needle and leaving the catheter;
    securing the window dressing to the catheter insertion site by adhesion of an adhesive to an area surrounding the catheter insertion site; and
    securing the catheter at the catheter insertion site via a securement portion of the window dressing.

16. The method of applying a window dressing and inserting a catheter of claim 15, wherein the ultrasound transmissive layer comprises a hydrogel.

17. The method of applying a window dressing and inserting a catheter of claim 15, wherein the adhesive comprises the ultrasound transmissive layer.

18. The method of applying a window dressing and inserting a catheter of claim 15, wherein the adhesive comprises an adhesive layer separate from the ultrasound transmissive layer.

* * * * *